United States Patent
Ernstberger

(10) Patent No.: US 8,905,754 B1
(45) Date of Patent: Dec. 9, 2014

(54) ORTHODONTIC BRACE FOR USE WITH A TEMPORARY ANCHORAGE DEVICE

(76) Inventor: Seth E. Ernstberger, New Albany, IN (US)

(*) Notice: Subject to any disclaimer, the term of this patent is extended or adjusted under 35 U.S.C. 154(b) by 348 days.

(21) Appl. No.: 12/881,116

(22) Filed: Sep. 13, 2010

(51) Int. Cl.
*A61C 7/00* (2006.01)

(52) U.S. Cl.
USPC .................................................. 433/18

(58) Field of Classification Search
CPC .............. A61C 7/00; A61C 7/08; A61C 7/10; A61C 7/12; A61C 7/14; A61C 7/145; A61C 7/36; A61C 5/007; A61C 8/0096
USPC ............ 433/8, 12, 18, 19, 20, 21, 22, 24, 2, 7
See application file for complete search history.

(56) References Cited

U.S. PATENT DOCUMENTS

| | | | | |
|---|---|---|---|---|
| 1,938,428 A * | 12/1933 | Johnson | | 433/20 |
| 2,705,367 A * | 4/1955 | Berke | | 433/8 |
| 3,798,773 A * | 3/1974 | Northcutt | | 433/19 |
| 5,352,116 A * | 10/1994 | West | | 433/19 |
| 5,401,168 A * | 3/1995 | Magill | | 433/18 |
| 5,562,445 A * | 10/1996 | DeVincenzo et al. | | 433/19 |
| 5,738,514 A * | 4/1998 | DeVincenzo et al. | | 433/19 |
| 5,846,074 A * | 12/1998 | Klapper | | 433/19 |
| 5,919,042 A * | 7/1999 | Williams | | 433/19 |
| 5,964,588 A * | 10/1999 | Cleary | | 433/19 |
| 6,089,862 A * | 7/2000 | Schutz | | 433/18 |
| 6,322,357 B1 * | 11/2001 | Vogt | | 433/19 |
| 6,595,774 B1 | 7/2003 | Risse | | |
| 6,655,959 B2 * | 12/2003 | Farzin-Nia et al. | | 433/18 |
| 6,719,557 B1 * | 4/2004 | Williams | | 433/19 |
| 6,877,982 B2 * | 4/2005 | Williams | | 433/19 |
| 7,416,409 B2 * | 8/2008 | Farber | | 433/18 |
| 7,578,672 B2 * | 8/2009 | Sheikh et al. | | 433/19 |
| 2003/0022125 A1 * | 1/2003 | Cleary | | 433/19 |
| 2003/0039939 A1 * | 2/2003 | Farzin-Nia et al. | | 433/18 |
| 2006/0024636 A1 * | 2/2006 | Bowman et al. | | 433/18 |
| 2007/0190477 A1 * | 8/2007 | Sheikh et al. | | 433/19 |
| 2007/0196781 A1 * | 8/2007 | Cope | | 433/18 |
| 2008/0020339 A1 * | 1/2008 | Papadopoulos | | 433/21 |
| 2008/0063995 A1 * | 3/2008 | Farzin-Nia et al. | | 433/22 |
| 2008/0138759 A1 * | 6/2008 | Kravitz et al. | | 433/21 |

OTHER PUBLICATIONS

Cope, Dr. Jason, Lecture Summary: Temporary Anchorage Devices in Orthodontics: Clinical Experimentation or Evidence-Based?; Jul. 19, 2006, 3 pages.

* cited by examiner

*Primary Examiner* — Cris L Rodriguez
*Assistant Examiner* — Justin O'Donnell
(74) *Attorney, Agent, or Firm* — Middleton Reutlinger; Robert H. Eichenberger; Scott W. Higdon

(57) ABSTRACT

Disclosed herein is an apparatus and method relating to bidirectionally anchoring an anchor tooth. The apparatus may include an adjustable length brace and may be utilized in conjunction with an orthodontic bracket and an orthodontic temporary anchorage device (TAD).

19 Claims, 10 Drawing Sheets

ORTHODONTIC BRACE FOR USE WITH A TEMPORARY ANCHORAGE DEVICE

TECHNICAL FIELD

The present invention is directed generally to the field of orthodontics. More particularly, various inventive methods and apparatus disclosed herein relate to an orthodontic brace for use with a temporary anchorage device.

BACKGROUND

Orthodontics is a specialized dental practice concerned with the movement of teeth to achieve an effective mating of the upper and lower teeth and/or concerned with providing a pleasing facial contour and/or pleasing appearance of the teeth. Tooth movement is generally accomplished by applying a force to the tooth in the direction of desired movement. A relatively long-term application of corrective force of the proper level will cause the root of the tooth to move within the supporting bone to enable tipping, rotation, translation, and/or other tooth movements needed to appropriately align the tooth.

Corrective force may be provided to a tooth via the force exerted by a stressed or activated elastic element coupled to an adjacent tooth. Elastic elements include elements such as, for example, a flexible metal wire, metal spring, coil spring assemblies, band, or similar devices. Recently, one or more such elements have been utilized in connection with temporary anchorage devices (TADs). A TAD is a device that is temporarily fixed to bone structure of a patient for the purpose of enhancing and providing sufficient orthodontic anchorage. The TAD remains substantially fixed in position in the bone structure and thereby provides substantially absolute anchorage. A TAD may include all variations of implants, screws, and pins and so forth placed for the purpose of providing orthodontic anchorage.

TADs are often used to indirectly anchor an anchor tooth while assisting in the movement of other teeth that are adjacent to the anchor tooth. In other words, the TADs may be utilized to hold an anchor tooth in its current position and that anchor tooth may be coupled to other adjacent teeth with a stressed or activated elastic element to thereby cause the adjacent tooth to move. Currently, indirect anchorage techniques utilizing a TAD involve only securing a wire ligature to the TAD and to the anchor tooth in order to prevent the anchor tooth from moving in a first direction, generally away from the TAD. The anchor tooth may be coupled to one or more other adjacent teeth utilizing elastic elements that function to move the other adjacent teeth in a second direction generally opposite the first direction. Thus, current indirect anchorage techniques utilize a TAD and wire ligature to restrict movement of the anchor tooth in only a single general direction. As a result, current indirect anchorage techniques only allow other adjacent teeth coupled to the anchor tooth to be moved in a single general direction with respect to the anchor tooth.

SUMMARY

The present disclosure is directed to inventive methods and apparatus for an orthodontic brace for use with a temporary anchorage device.

Generally, in one aspect, an orthodontic brace for use in conjunction with an orthodontic bracket and an orthodontic temporary anchorage device is provided. The orthodontic brace includes a rigid shaft portion, a temporary anchorage device engagement structure, and an orthodontic bracket engagement structure. The rigid shaft portion has a shaft first end, a shaft second end, a shaft length extending from the shaft first end to the shaft second end, and at least one interior wire pathway extending from proximal the shaft first end to proximal the shaft second end. The shaft length is fixedly adjustable to a desired length of a plurality of lengths. The temporary anchorage device engagement structure is the the shaft first end, has at least one temporary anchorage device notch, and is sized and configured to engage the temporary anchorage device. The orthodontic bracket engagement structure is proximal the shaft second end, has at least one orthodontic bracket notch, and is sized and configured to engage the orthodontic bracket.

In some embodiments the rigid shaft includes a rigid outer shaft telescopically receiving a rigid inner shaft. In some versions of those embodiments at least a portion of the rigid outer shaft is interiorly threaded and at last a portion of the rigid inner shaft is exteriorly threaded. In some versions of those embodiments the rigid outer shaft is crimpable.

In some embodiments the interior wire pathway extends from the first end to the second end.

In some embodiments a wire is provided extending through the interior wire pathway. In some versions of those embodiments the wire has a closed loop portion extending from the interior wire pathway. In some versions of those embodiments the closed loop portion extends from the interior wire pathway proximal the first end. In some versions of those embodiments the wire has a first wire end and a second wire end each extending from the interior wire pathway proximal the second end.

In some embodiments the rigid shaft portion does not completely surround the wire pathway. In some versions of those embodiments the rigid shaft portion may optionally have a generally C shaped cross section.

Generally, in another aspect a system for bidirectionally bracing an anchor tooth is provided. The system includes an orthodontic bracket, an orthodontic temporary anchorage device, and a brace. The brace has a rigid shaft portion with a first end and a second end, a temporary anchorage device engagement structure proximal the first end, and an orthodontic bracket engagement structure proximal the second end. The rigid shaft portion has a shaft length extending from the shaft first end to the shaft second end. The shaft length is fixedly adjustable to a desired length of a plurality of lengths. The temporary anchorage device engagement structure is sized and configured to engage the temporary anchorage device. The orthodontic bracket engagement structure is sized and configured to engage the orthodontic bracket.

In some embodiments the temporary anchorage device engagement structure includes at least one temporary anchorage device engagement structure notch. In some versions of those embodiments the temporary anchorage device engagement structure includes an extension portion extending from the temporary anchorage device engagement structure notch in a direction away from the second end, wherein the extension portion and the notch sized and configured to substantially surround the temporary anchorage device.

In some embodiments the system further comprises a wire. In some versions of those embodiments the rigid shaft portion has a wire pathway extending therethrough. The wire pathway at least partially houses the wire. In some versions of those embodiments the wire pathway extends from the first end to the second end of the rigid shaft portion.

In some embodiments the rigid shaft portion includes a rigid outer shaft telescopically receiving a rigid inner shaft.

In some embodiments the orthodontic bracket includes an orthodontic bracket hook and wherein the orthodontic bracket engagement structure is sized and configured to engage the orthodontic bracket hook.

Generally, in another aspect a method of bidirectionally anchoring an anchor tooth, is provided. The method may include the steps of: providing a brace having an adjustable length; securing a first wire portion to a temporary anchorage device coupled to boney structure of a patient; securing a second wire portion to an orthodontic bracket coupled to a tooth of the patient; and fixedly adjusting the adjustable length of the brace to a set length. When the adjustable brace is at the set length, the adjustable brace is in contact with the orthodontic bracket and the temporary anchorage device. Also, the second wire portion secured to the orthodontic bracket is substantially taut and the first wire portion secured to the temporary anchorage device is substantially taut.

In some embodiments the first wire portion extends from the brace when the first wire portion is secured to the temporary anchorage device.

In some embodiments the brace includes an outer shaft telescopically receiving an inner shaft. In some versions of those embodiments the length of the brace is fixedly adjusted following securing of the first wire portion to the temporary anchorage device and securing of the second wire portion to the orthodontic bracket.

In some embodiments the first wire portion and the second wire portion are part of a single wire and extend through at least a portion of the brace.

It should be appreciated that all combinations of the foregoing concepts and additional concepts discussed in greater detail below (provided such concepts are not mutually inconsistent) are contemplated as being part of the inventive subject matter disclosed herein. For example, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

In the following detailed description, for purposes of explanation and not limitation, representative embodiments disclosing specific details are set forth in order to provide a thorough understanding of the claimed invention. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the claimed invention.

Figure 1A:
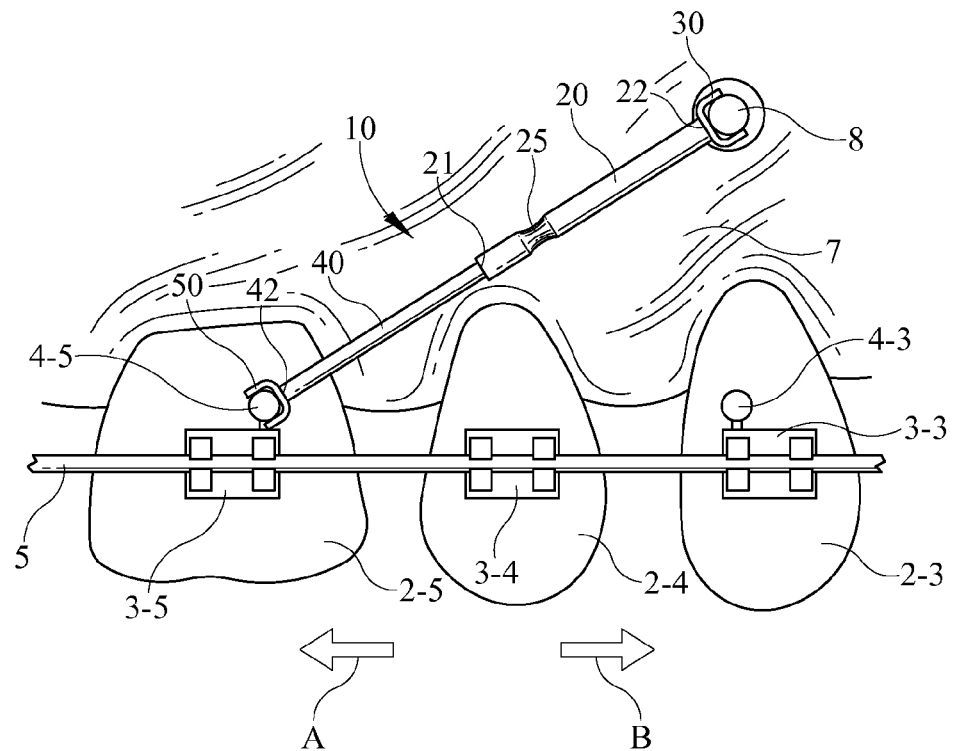
FIG. 1A illustrates a first embodiment of an orthodontic system for bracing an anchor tooth; the system is shown in use in conjunction with upper teeth of a patient in a first configuration.
Figure 1B:
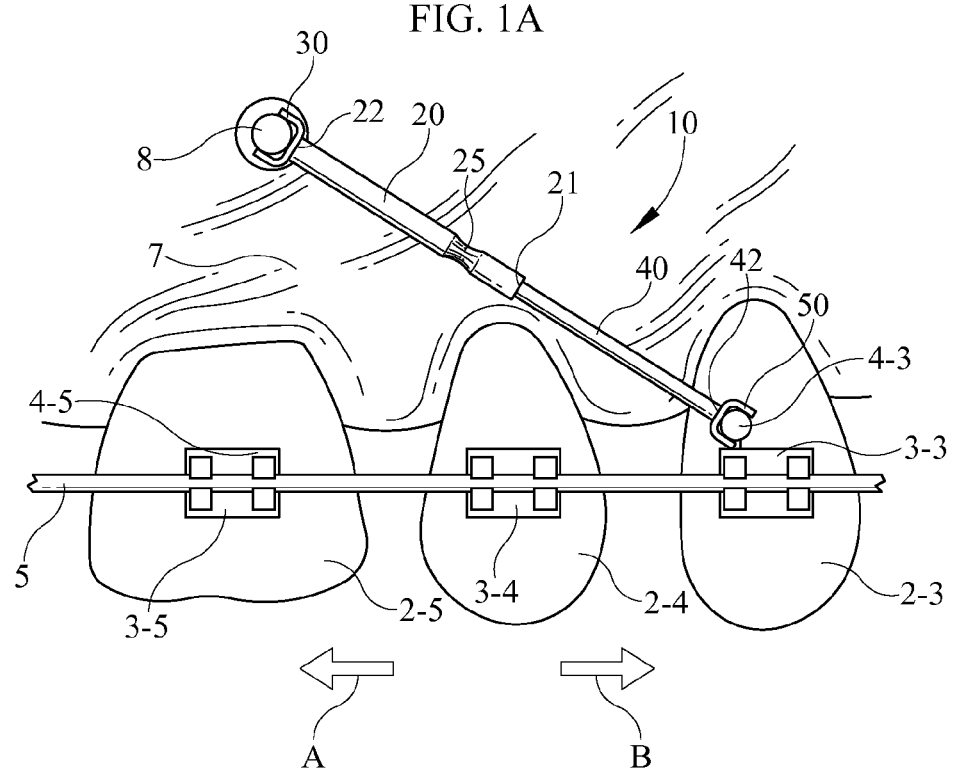
FIG. 1B illustrates the first embodiment of an orthodontic system in use in upper teeth of a patient in a second configuration.

Referring now to the figures, various embodiments of a method and apparatus related to an orthodontic brace for use with a temporary anchorage device are described in detail. Referring initially to FIG. 1A and FIG. 1B, an orthodontic system for bracing an anchor tooth is depicted. The orthodontic system is shown in use in conjunction with upper teeth 2-3, 2-4, and 2-5. The upper teeth 2-3, 2-4, and 2-5 have brackets 3-3, 3-4, and 3-5, respectively, coupled thereto. An archwire 5 is coupled to and extends between the brackets 3-3, 3-4, and 3-5. The bracket 3-3 has a bracket extension 4-3 extending upwardly therefrom and the bracket 3-5 likewise has a bracket extension 4-5 extending upwardly therefrom. A temporary anchorage device (TAD) 8 is substantially fixedly implanted in boney structure of the patient through the gingiva 7 of the patient. In FIG. 1A the TAD 8 is implanted upward of and adjacent to tooth 2-3 and tooth 2-4 and in FIG. 1B the TAD 8 is implanted upward of and adjacent to tooth 2-5.

In FIG. 1A an orthodontic brace 10 of the orthodontic system extends between TAD 8 and the bracket extension 4-5. The orthodontic brace 10 includes a rigid shaft portion having a rigid outer shaft 20 having an outer shaft first end 21 and an outer shaft second end 22. The outer shaft 20 telescopically receives a rigid inner shaft 40 having an inner shaft first end (telescopically received in the outer shaft 20 in FIG. 1A) and an inner shaft second end 42. The rigid outer shaft 20 has a TAD engagement structure 30 coupled to the outer shaft second end 22 thereof. The rigid inner shaft 40 has a bracket engagement structure 50 coupled to the inner shaft second end 42 thereof. As will be described in additional detail herein, the positioning of the rigid outer shaft 20 along the rigid inner shaft 40 may be fixedly adjustable to a desired positioning. In other words, the distance between the outer shaft second end 22 and the inner shaft second end 42 may be fixedly adjusted.

In FIG. 1A the positioning of the rigid outer shaft 20 along the rigid inner shaft 40 is fixed via a crimp 25 on rigid outer shaft 20. The crimp 25 also extends through to rigid inner shaft 40 where it is telescopically received in rigid outer shaft 20 to thereby fixedly couple the positioning of rigid inner shaft 40 with respect to rigid outer shaft 20. Rigid inner shaft 40 and rigid outer shaft 20 are fixed at a position such that the TAD engagement structure 30 is in contact with TAD 8 and the bracket engagement structure 50 is in contact with bracket extension 4-5. Accordingly, by virtue of the orthodontic brace 10, bracket extension 4-5, bracket 3-5, and tooth 2-5 are restricted by the orthodontic brace 10 from moving in a first direction generally indicated by arrow B. Prior to being crimped, the rigid inner shaft 40 is telescopically adjustable with respect to the rigid outer shaft 20. Optionally, the rigid inner shaft 40 may be snugly, but adjustably telescopically received by the rigid outer shaft 20 prior to being crimped.

As will be described in additional detail herein, the orthodontic brace 10 also has a wire 60 extending therethrough from proximal the outer shaft second end 22 to proximal the inner shaft second end 42. The wire 60 exits the brace 10 proximal the outer shaft second end 22, where it is securely coupled to the TAD 8. The wire 60 also exits the brace 10 proximal the inner shaft second end 42, where it is securely coupled the bracket extension 4-5. The wire 60 is taut between its coupling with the bracket extension 4-5 and the TAD 8. Accordingly, by virtue of the wire 60, extension 4-5, bracket 3-5, and tooth 2-5 are restricted from moving in a second direction that is generally indicated by arrow A.

In FIG. 1A the tooth 2-5 functions as an anchor tooth. As a result of the orthodontic brace 10 and the wire 60 extending therethrough, the tooth 2-5 is substantially restricted from movement in either the first direction generally indicated by arrow B or the second direction generally indicated by arrow A. Accordingly, one or more adjacent teeth (e.g., tooth 2-4 and/or tooth 2-3) may be directly or indirectly coupled to tooth 2-5 with a stressed or activated elastic element that applies force in a direction that has a component in the first direction or in a direction that has a component in the second direction. For example, a closing loop may be coupled to tooth 2-5 and to tooth 2-4 to thereby apply force to tooth 2-4 having a component in the second direction indicated by arrow A. Also, for example, a compressed open coil spring may be coupled to tooth 2-5 and to tooth 2-4 to thereby apply force to tooth 2-4 having a component in the first direction indicated by arrow B. Other elastic elements may additionally or alternatively be directly or indirectly coupled to tooth 2-5 and/or other adjacent teeth, such as, for example, a flexible metal wire, metal spring, coil spring assemblies, and/or a band.

In FIG. 1B the TAD 8 of the orthodontic system is illustrated implanted upward of and adjacent to the tooth 2-5. The orthodontic brace 10 extends between TAD 8 and the bracket extension 4-3. The positioning of rigid outer shaft 20 along the rigid inner shaft 40 is fixed via a crimp 25. The rigid inner shaft 40 and the rigid outer shaft 20 are fixed at a position such that the TAD engagement structure 30 is in contact with TAD 8 and the bracket engagement structure 50 is in contact with bracket extension 4-3. Accordingly, bracket extension 4-3, bracket 3-3, and tooth 2-3 are restricted by the orthodontic brace 10 from moving in the second direction generally indicated by arrow A. As described herein, the orthodontic brace 10 also has a wire 60 extending therethrough from proximal the outer shaft second end 22 to proximal the inner shaft second end 42. The wire 60 extends from the brace 10 and is securely coupled to the bracket extension 4-3, is securely coupled to the TAD 8, and is taut therebetween. Accordingly, extension 4-3, bracket 3-3, and tooth 2-3 are restricted by the wire 60 from moving in the first direction generally indicated by arrow B.

In FIG. 1B the tooth 2-3 functions as an anchor tooth. As a result of the orthodontic brace 10 and the wire 60 extending therethrough, the tooth 2-3 is substantially restricted from movement in either the first direction generally indicated by arrow B or the second direction generally indicated by arrow A. Accordingly, one or more adjacent teeth (e.g., tooth 2-4 and/or tooth 2-5) may be directly or indirectly coupled to tooth 2-3 with a stressed or activated elastic element that applies force in a direction that has a component in the first direction or in a direction that has a component in the second direction.

One of ordinary skill in the art, having had the benefit of the present disclosure, will recognize that TADs that are distinct from TAD 8 in one or more respect may be utilized in the orthodontic system. For example, TADs may be utilized that have a different shape, a different material configuration, a different means for coupling to a patient, and/or utilize a different method to be coupled to a patient. One of ordinary skill in the art, having had the benefit of the present disclosure, will also recognize that brackets that are distinct from brackets 3-3, 3-4, and 3-5 in one or more respect may be utilized in the orthodontic system. For example, brackets may be utilized that have a different shape, a different material configuration, different bracket extensions extending therefrom, no bracket extensions extending therefrom, a different means for coupling to a patient, and/or utilize a different method to be coupled to a patient.

Figure 2A:
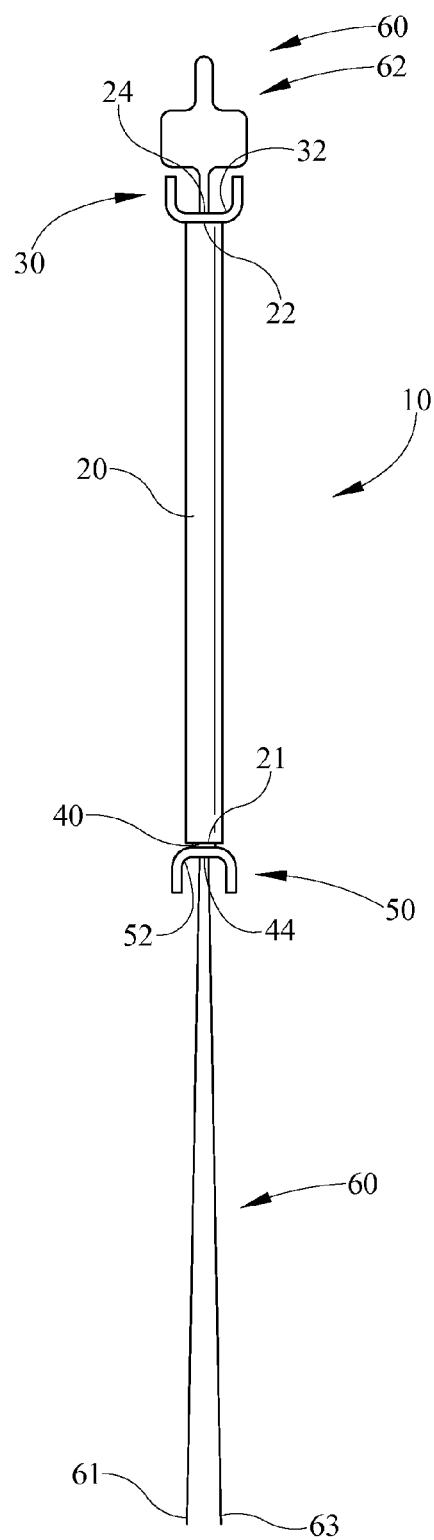
FIG. 2A illustrates an orthodontic brace and a wire of the first embodiment of an orthodontic system; the orthodontic brace is in a contracted state.
Figure 2B:
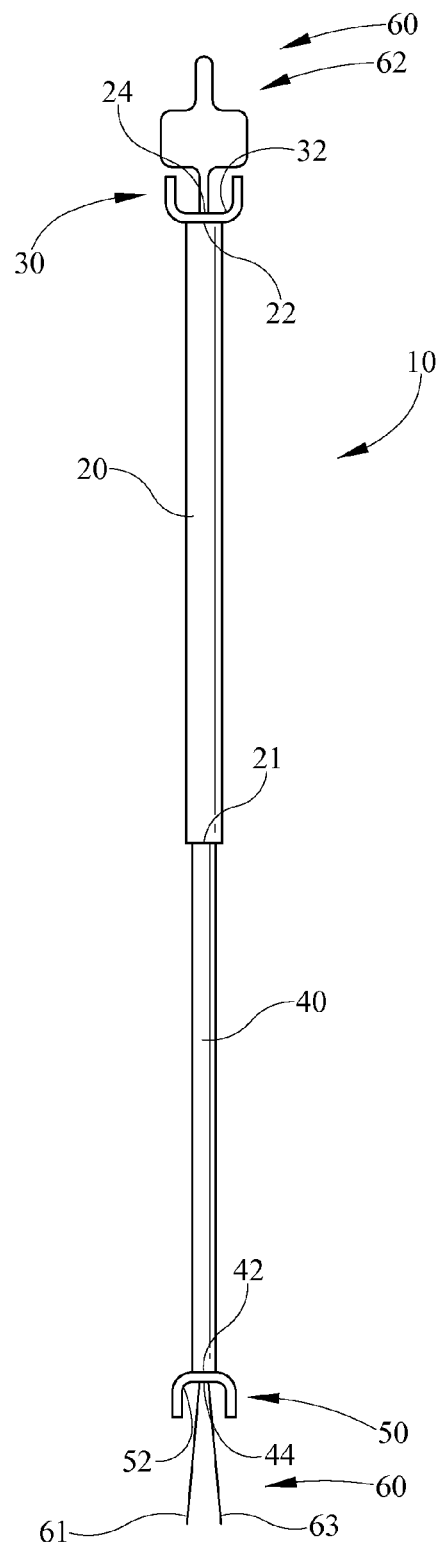
FIG. 2B illustrates the orthodontic brace and a wire of the first embodiment of an orthodontic system; the orthodontic brace is in a fully expanded state.

Referring to FIGS. 2A and 2B, the orthodontic brace 10 is depicted in a contracted state (FIG. 2A) and a fully expanded state (FIG. 2B). In the contracted state of FIG. 2A, the rigid inner shaft 40 is substantially completely telescopically received by the rigid outer shaft 20. In the expanded state of FIG. 2B, the first end of the rigid inner shaft 40 is barely received in the rigid outer shaft 20 and barely extends past the first end 21 thereof. The positioning of the rigid outer shaft 20 with respect to the rigid inner shaft 40 may be fixed at the contracted state of FIG. 2A, the fully expanded state of FIG. 2B or at any desired of a plurality of positions therebetween by crimping rigid outer shaft 20 and rigid inner shaft 40. The rigid outer shaft 20 and rigid inner shaft 40 may be crimped utilizing, for example, a crimping plier with appropriately sized beaks. Optionally, in some embodiments rigid outer shaft 20 and/or rigid inner shaft 40 may contain stop structure to limit the extent to which outer shaft second end 22 and inner shaft second end 42 may be moved apart and/or toward one another. For example, rigid inner shaft 40 may have one or more flange portions extending radially from an exterior surface thereof that interact with one or more flange portions extending inward from an interior surface of rigid outer shaft 20.

Although crimping rigid outer shaft 20 and rigid inner shaft 40 to fix their positioning at a desired of a plurality of positions is depicted in various Figures, alternative or additional methods and/or structure may be utilized to fix the positioning of rigid outer shaft 20 and rigid inner shaft 40 with respect to one another. For example, in some embodiments a locking nut may be provided around outer shaft 20 and inner shaft 40 that interacts with external threads on at least one of outer shaft 20 and inner shaft 40 to enable fixation of the position of outer shaft 20 with respect to inner shaft 40. Also, for example, in some embodiments a compression nut may be provided around outer shaft and inner shaft 40 that compressingly contacts at least one of outer shaft 20 and inner shaft 40 to enable fixation of the position of outer shaft 20 with respect to inner shaft 40. Also, for example, in some embodiments outer shaft 20 and inner shaft 40 may be soldered to one another to provide fixation of the position of outer shaft 20 with respect to inner shaft 40.

In FIGS. 2A and 2B, a formed closed loop portion 62 of a wire 60 extends from a wire opening 24 through the second end 22 of the rigid outer shaft 20. The TAD engagement structure 30 includes a generally U shaped notch portion 32 that flanks a portion of the closed loop portion 62. The closed loop portion 62 is sized and configured to surround and be engagingly coupled to the TAD 8 upon being pulled taut by a user. The wire 60 extends through a longitudinally extending wire pathway that extends from wire opening 24 of rigid outer shaft 20 to a wire opening 44 of rigid inner shaft 40. The wire 60 includes a first wire end 61 and a second wire end 63 that extend from the wire opening 44. The wire 60 proximal the first wire end 61 and the second wire end 63 is sized and configured to be engagingly coupled to brackets 3-3, 3-4, and 3-5, bracket extensions 4-3, 4-4, and 4-5, and/or other structural components that may be directly or indirectly coupled to a tooth. The bracket engagement structure 50 includes a generally U shaped notch portion 52 that flanks a portion of the wire 60 where it extends from wire opening 44.

Figure 3A:
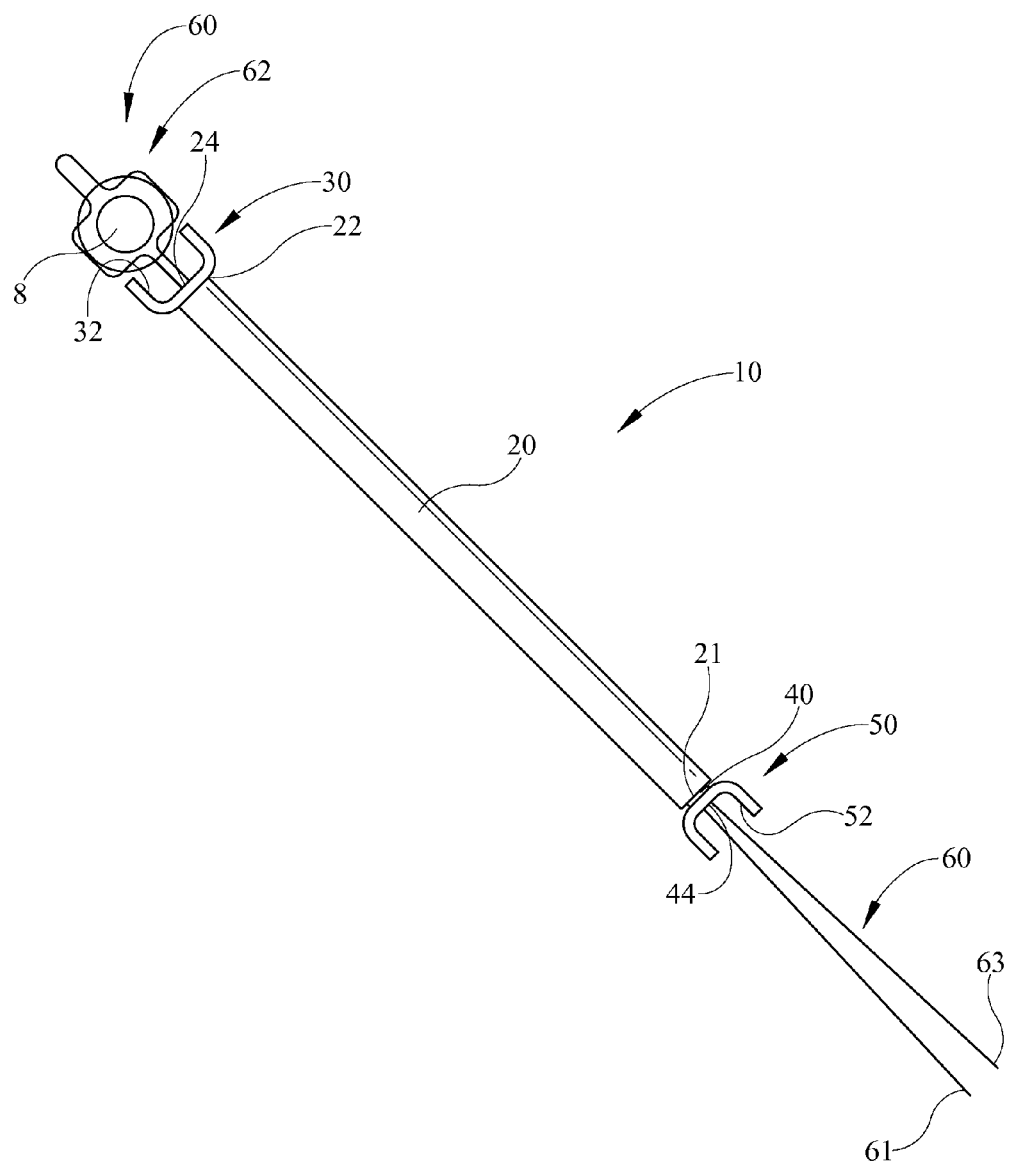
FIG. 3A illustrates the orthodontic brace of the first embodiment of an orthodontic system; a closed loop portion of the wire extending through the orthodontic brace is shown placed about a temporary anchorage device of the first embodiment of an orthodontic system.
Figure 3B:
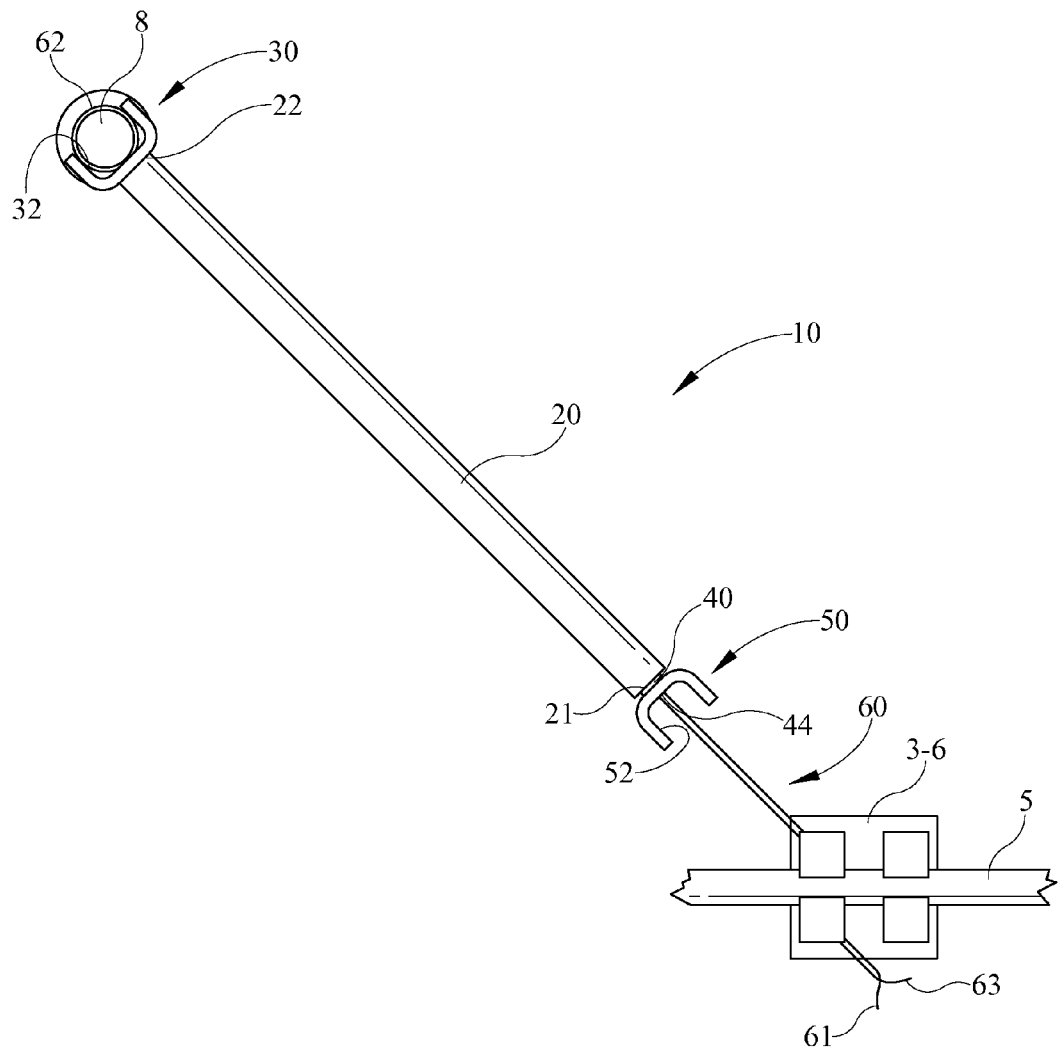
FIG. 3B illustrates the first embodiment of an orthodontic system; a closed loop portion of the wire is shown secured to the temporary anchorage device and a temporary anchorage device engagement structure of the orthodontic brace is shown in contact with the temporary anchorage device; an open end portion of the wire is shown secured to an orthodontic bracket of the first embodiment of an orthodontic system.
Figure 3C:
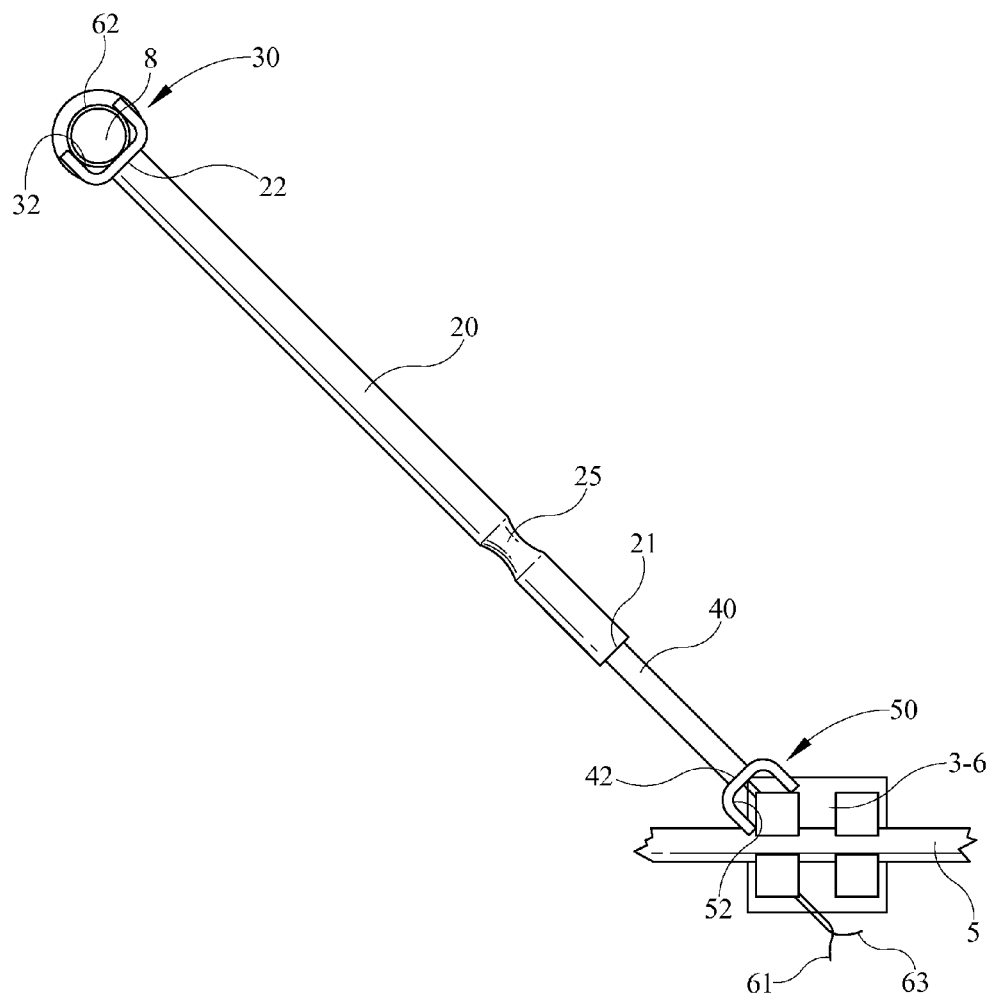
FIG. 3C illustrates the first embodiment of an orthodontic system; a closed loop portion of the wire is shown secured to the temporary anchorage device, a temporary anchorage device engagement structure of the orthodontic brace is shown in contact with the temporary anchorage device, an open end portion of the wire is shown secured to the orthodontic bracket, and a bracket engagement structure of the orthodontic brace is shown in contact with the orthodontic bracket.

Referring to FIGS. 3A-3C, an embodiment of bidirectionally anchoring an anchor tooth utilizing the orthodontic brace 10 is described in detail. FIG. 3A illustrates the orthodontic brace 10 and the TAD 8 of the first embodiment of the orthodontic system. The orthodontic brace 10 is in a contracted position and the closed loop portion 62 of the wire 60 of the orthodontic brace 10 is shown placed about the TAD 8. In FIG. 3B the closed loop portion 62 of the wire 60 is substantially secured to the TAD 8 and the TAD engagement structure 30 is in contact with the TAD 8. The closed loop portion 62 may be secured to the TAD 8 by pulling on the first and second wire end 61 and 63 to thereby tighten the closed loop portion 62 about the TAD 8. The TAD engagement structure 30 may be in contact with the TAD 8 by slidingly moving the rigid outer shaft 20 toward the TAD 8.

In FIG. 3B the first wire end 61 and the second wire end 63 have been secured to an anchor tooth bracket 3-6. The first wire end 61 and the second wire end 63 have been secured to anchor tooth bracket 3-6 such that the portion of wire 60 extending between bracket 3-6 and TAD 8 is substantially taut.

In FIG. 3C the rigid inner shaft 40 has been telescopically adjusted such that the bracket engagement structure 50 is in contact with a portion of the bracket 3-6. A crimp 25 has also been placed to fix the positioning of the rigid inner shaft 40 with respect to the rigid outer shaft 20. In some embodiments a spring may be provided internally of the orthodontic brace 10 that contacts the rigid outer shaft 20 and the rigid inner shaft 40. The internal spring may provide active force on the outer shaft 20 and the rigid inner shaft 40 in a direction that forces the second ends 22 and 42 away from each other. The internal spring may be used in lieu of a crimp or may be used to ensure contact between the TAD engagement structure 30 and TAD 8 and the bracket engagement structure 50 and the bracket 3-6 occurs prior to placing of the crimp 25.

In alternative embodiments, the steps of the first embodiment of bidirectionally anchoring an anchor tooth may be performed in a different order. For example, in some embodiments the wire 60 extending through the orthodontic brace 10 may be coupled to a bracket prior to being coupled to a TAD. Also, for example, in some embodiments bracket engagement structure 50 may be engaged against a bracket prior to, or simultaneous with, TAD engagement structure 30 being engaged against a TAD. Also, for example, in some embodiments a closed loop portion of a wire may be coupled to a bracket and a non-closed loop portion may be coupled to a TAD. In some embodiments the wire 60 extending through the orthodontic brace 10 may be a threaded ligature tie. In versions of those embodiments the threaded ligature tie may be, for example, 0.010" stainless steel. In some embodiments the orthodontic brace 10 and the engagement structures 30 and 50 thereof may comprise stainless steel and/or Nitinol.

Figure 4:
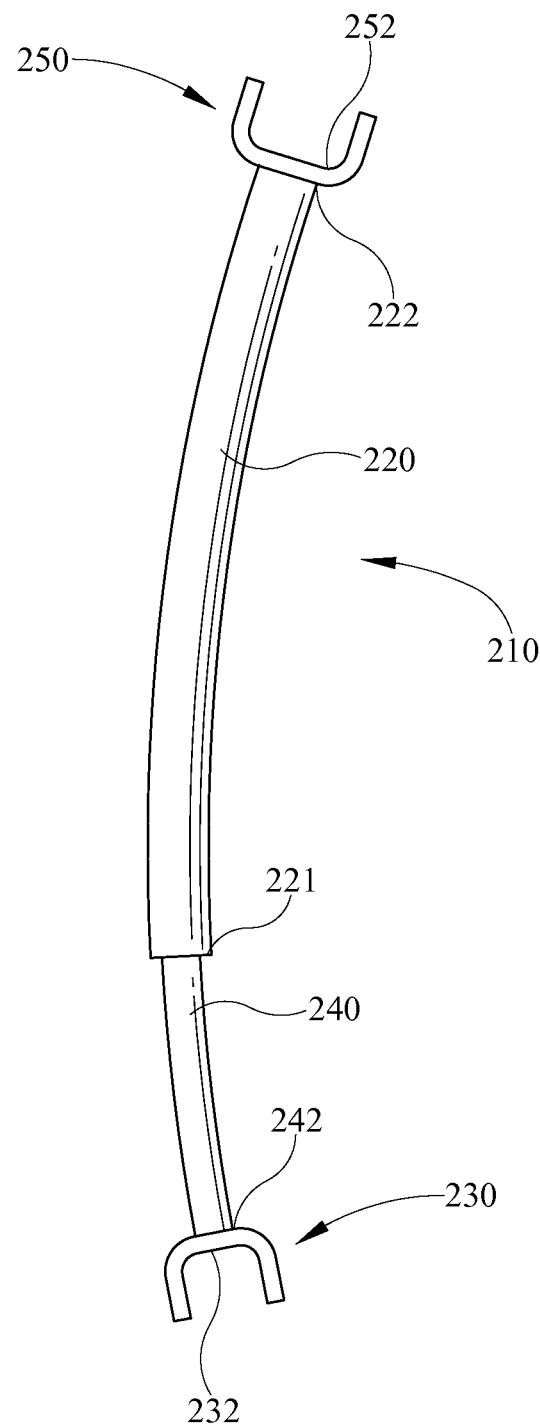
FIG. 4 illustrates a second embodiment of an orthodontic brace.

Referring to FIG. 4, a second embodiment of an orthodontic brace 210 is illustrated. The orthodontic brace 210 has a rigid outer shaft 220 that telescopically receives a rigid inner shaft 240. The rigid outer shaft 220 includes a first end 221 and a second end 222. The rigid inner shaft 240 includes a first end (received within rigid outer shaft 220) and a second end 242. A TAD engagement structure 230 is coupled to the second end 242 of the rigid inner shaft 240 and a bracket engagement structure 250 is coupled to the second end 222 of the rigid outer shaft 220. In this embodiment the TAD engagement structure 230 is on the rigid inner shaft 240 and the bracket engagement structure 250 is on the rigid outer shaft 220. The TAD engagement structure 230 has a notch 232 therein and the bracket engagement structure 250 has a notch 252 therein. The rigid outer shaft 220 and the rigid inner shaft 240 share a substantially common curvature and provide for a curved orthodontic brace 210 having an adjustable length.

The positioning of the rigid inner shaft 240 with respect to the rigid outer shaft 220 is unidirectionally adjustable to thereby cause the distance between the second 222 end of the rigid outer shaft 220 and the second end 242 of the rigid inner shaft 240 to be unidirectionally increased. The device that permits unidirectional adjustability may be a passive mechanical device that permits motion in one direction and resists motion in the opposite direction. The positions at which the device resists motion may be continuously variable or may comprise a finite number of discrete positions. It is possible that unidirectionally adjustable braces which operate with a finite number of discrete positions may still permit bidirectional motion in the distance between adjacent discrete positions. The device that permits unidirectional adjustability may be such that when the positioning between the second ends 222 and 242 is increased, that increased positioning is retained. It is possible that the positioning between the second ends 222 and 242 may occur at any one of an infinite number of positions (continuously variable), such as gripping by friction on the surface of a smooth rod (e.g., frictional elements on the interior surface of rigid outer shaft 220 that engage the outer surface of rigid inner shaft 240). Alternatively, it is possible that the positioning between the second ends 222 and 242 may have increments of acceptable length positions, such that if the positioning between the second ends 222 and 242 is lengthened, it can slip back to the nearest incremental stopping (e.g., a rack and pawl configuration on the interior surface of rigid outer shaft 220 and the outer surface of rigid inner shaft 240). In alternative embodiments, the adjustability of the positioning between the second ends 222 and 242 may experience no slip-back at all. Optionally, a crimp may be utilized to prevent further unidirectional increase of the distance between outer shaft second end 222 and inner shaft second end 242. In alternative embodiments the positioning between the second ends 222 and 242 may be bidirectionally adjustable. Also, unidirectional adjustability may optionally be implemented in other embodiments described herein.

Figure 5C:
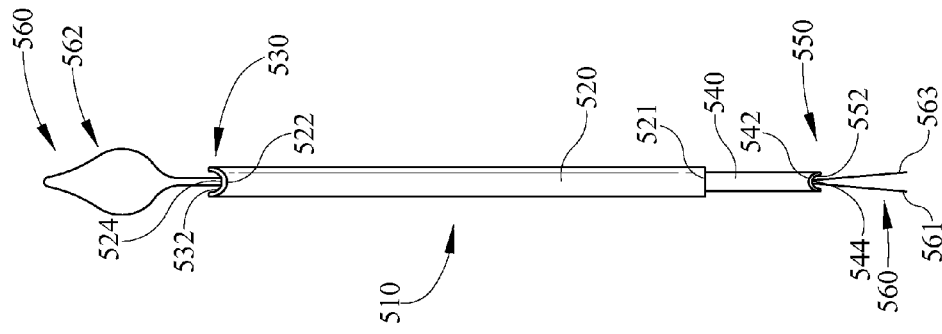
FIG. 5C illustrates a fifth embodiment of an orthodontic brace.
Figure 5B:
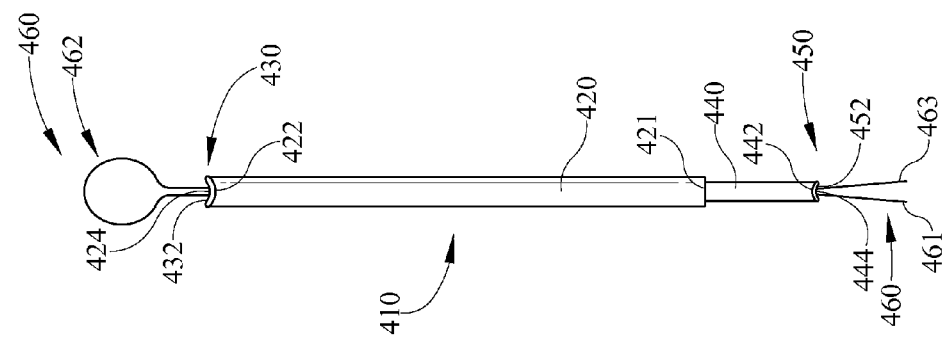
FIG. 5B illustrates a fourth embodiment of an orthodontic brace.
Figure 5A:
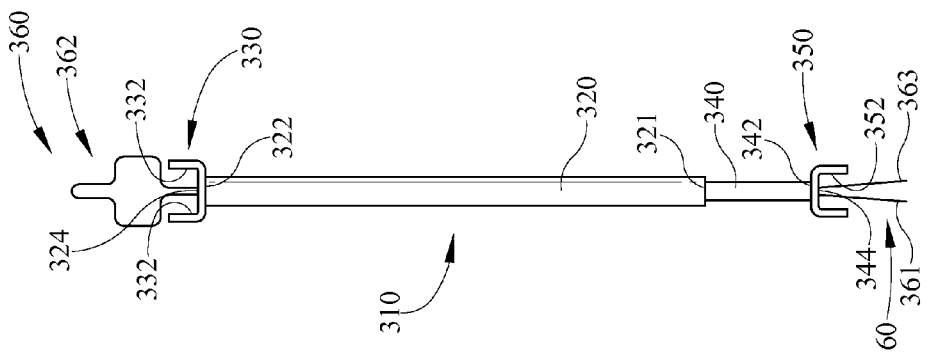
FIG. 5A illustrates a third embodiment of an orthodontic brace.

Referring to FIG. 5A, a third embodiment of an orthodontic brace 310 is illustrated. The orthodontic brace 310 is similar to the first embodiment of the orthodontic brace 10 and like reference numbers between the two refer to like elements (e.g., reference numbers 320, 321, 322, 324, 340, 342, 344, 350, 352, 360, 361, and 363 refer to like elements of reference numbers 20, 21, 22, 24, 40, 42, 44, 50, 52, 60, 61, and 63, respectively, of orthodontic brace 10). However, the TAD engagement structure 330 of the orthodontic brace 310 has a shape and configuration that is unique from TAD engagement structure 30 of the orthodontic brace 10. For example, the TAD engagement structure 330 is still generally U shaped, but has a notch 332 that is defined by structure that is slightly more linear than the substantially rounded structure segments that define notch 32.

Referring to FIG. 5B, a fourth embodiment of an orthodontic brace 410 is illustrated. The orthodontic brace 410 is similar to the first embodiment of the orthodontic brace 10 and like reference numbers between the two refer to like elements (e.g., reference numbers 421, 424, 444, 461, and 463 refer to like elements of reference numbers 21, 24, 44, 61, and 63, respectively, of orthodontic brace 10). However, distinctions between orthodontic brace 410 and orthodontic brace 10 exist. For example, the TAD engagement structure 430 of the orthodontic brace 410 has a shape and configuration that is unique from TAD engagement structure 30 of the orthodontic brace 10. For example, the TAD engagement structure 430 has a notch 432 that is shallower than the notch 32 and the engagement structure 430 is coupled to a notch that is integrally formed in the second end 422 of rigid outer shaft 420. Also, for example, the bracket engagement structure 450 has a shape and configuration that is unique from the bracket engagement structure 50. The bracket engagement structure 450 has a notch 452 that is shallower than the notch 52 and the engagement structure 450 is coupled to a notch that is integrally formed in the second end 442 of rigid inner shaft 440. Also, for example, the closed loop portion 462 of the wire 460 has a balloon shape that is distinct from the shape of closed loop portion 62.

Referring to FIG. 5C, a fifth embodiment of an orthodontic brace 510 is illustrated. The orthodontic brace 510 is similar to the first embodiment of the orthodontic brace 10 and like reference numbers between the two refer to like elements (e.g., reference numbers 521, 524, 532, 544, 561, and 563 refer to like elements of reference numbers 21, 24, 32, 44, 61, and 63, respectively, of orthodontic brace 10). However, distinctions between orthodontic brace 510 and orthodontic brace 10 exist. For example, the TAD engagement structure 530 of the orthodontic brace 510 has a shape and configuration that is unique from TAD engagement structure 30 of the orthodontic brace 10. For example, the TAD engagement structure 530 is still generally U shaped, but has a size and shape that is distinct from notch 32. Moreover, for example, the TAD engagement structure 530 is coupled to a notch that is integrally formed in the second end 522 of rigid outer shaft 520. Also, the bracket engagement structure 550 has a shape and configuration that is unique from the bracket engagement structure 50. For example, the bracket engagement structure 550 is still generally U shaped, but has a notch 552 that is coupled to a notch that is integrally formed in the second end 542 of rigid inner shaft 540. Also, for example, the closed loop portion 562 of the wire 560 has a flame shape that is distinct from the shape of closed loop portion 62.

Figure 5F:
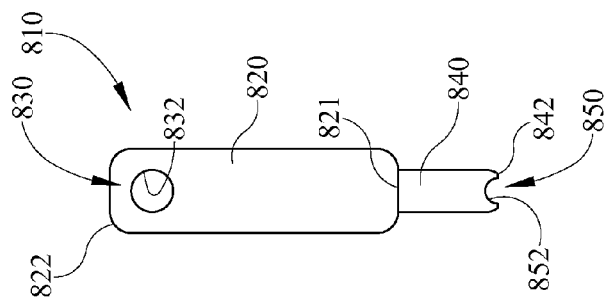
FIG. 5F illustrates an eighth embodiment of an orthodontic brace
Figure 5E:
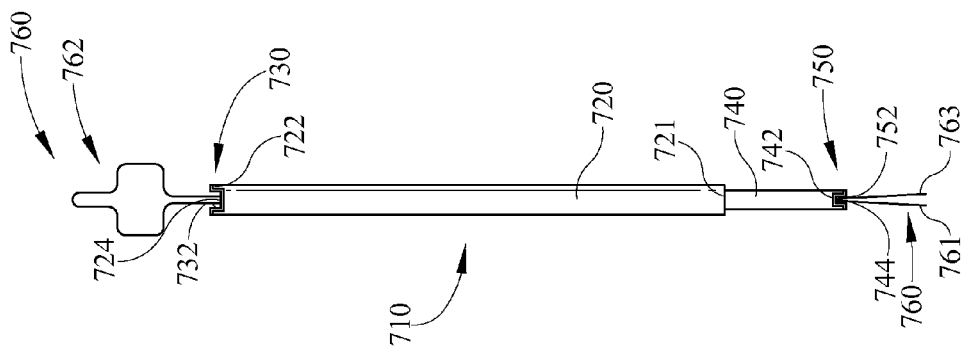
FIG. 5E illustrates a seventh embodiment of an orthodontic brace.
Figure 5D:
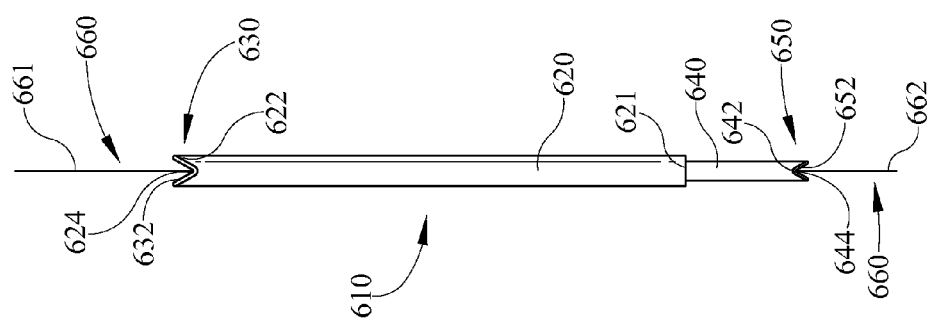
FIG. 5D illustrates a sixth embodiment of an orthodontic brace.

Referring to FIG. 5D, a sixth embodiment of an orthodontic brace 610 is illustrated. The orthodontic brace 610 is similar to the first embodiment of the orthodontic brace 10 and like reference numbers between the two refer to like elements (e.g., reference numbers 621, 632, and 652 refer to like elements of reference numbers 21, 32, and 52, respectively, of orthodontic brace 10). However, distinctions between orthodontic brace 610 and orthodontic brace 10 exist. For example, the TAD engagement structure 630 of the orthodontic brace 610 has a shape and configuration that is unique from TAD engagement structure 30 of the orthodontic brace 10. For example, the TAD engagement structure 630 is generally V shaped and is coupled to a generally V shaped notch that is integrally formed in the second end 622 of rigid outer shaft 620. Also, for example, the bracket engagement structure 650 has a shape and configuration that is unique from the bracket engagement structure 50. For example, the bracket engagement structure 650 is generally V shaped and is coupled to a generally V shaped notch that is integrally formed in the second end 642 of rigid inner shaft 640. Also, for example, the wire 660 extending through the orthodontic brace 610 has a wire first end 661 that extends through an opening 624 in the rigid outer shaft 620 and a wire second end 662 that extends through an opening 644 in the rigid inner shaft 640. The wire first end 661 may be securely coupled to a TAD or a bracket and the wire second end 662 may be securely coupled to a TAD or a bracket.

Referring to FIG. 5E, a seventh embodiment of an orthodontic brace 710 is illustrated. The orthodontic brace 710 is similar to the first embodiment of the orthodontic brace 10 and like reference numbers between the two refer to like elements (e.g., reference numbers 721, 724, 732, 744, 752, 760, 761, 762, and 763 refer to like elements of reference numbers 21, 24, 32, 44, 52, 60, 61, 62, and 63, respectively, of orthodontic brace 10). However, distinctions between orthodontic brace 710 and orthodontic brace 10 exist. For example, the TAD engagement structure 730 of the orthodontic brace 710 has a shape and configuration that is unique from TAD engagement structure 30 of the orthodontic brace 10. For example, the TAD engagement structure 730 is still generally U shaped, but is coupled to and integrally formed in a notch in the second end 722 of the rigid outer shaft 720. Also, for example, the bracket engagement structure 750 has a shape and configuration that is unique from the bracket engagement structure 50 of the orthodontic brace 10. For example, the bracket engagement structure 750 is coupled to and integrally formed in the second end 742 of rigid inner shaft 740.

Referring to FIG. 5F, an eighth embodiment of an orthodontic brace 810 is illustrated. The orthodontic brace 810 is similar to the first embodiment of the orthodontic brace 10 and like reference numbers between the two refer to like elements (e.g., reference number 821 refers to like element of reference number 21). However, distinctions between orthodontic brace 810 and orthodontic brace 10 exist. For example, the TAD engagement structure 830 of the orthodontic brace 810 has a shape and configuration that is unique from TAD engagement structure 30 of the orthodontic brace 10. For example, the TAD engagement structure 830 includes an annular notch 832 integrally formed in the rigid outer shaft 820 proximal the second end 822 thereof. The annular notch 832 may be sized and configured to be placeable over the head of a TAD. In some embodiments the annular notch 832 may additionally or alternatively be configured to be placeable over at least a portion of a bracket (e.g., a bracket extension). Also, in some embodiments the annular notch 832 may additionally or alternatively be configured to receive an archwire. For example, an archwire may be threaded through the annular notch 832 during installation of the archwire. Also, in some embodiments the notch 832 may have a different non-annular geometric configuration.

With continuing reference to FIG. 5F, the bracket engagement structure 850 also has a shape and configuration that is unique from the bracket engagement structure 50. For example, the bracket engagement structure 850 is still generally U shaped, but has a notch 852 that is integrally formed in the second end 842 of rigid inner shaft 840. Also, the orthodontic brace 810 is not provided with a wire in the depicted embodiment. Optionally, a wire may be provided separate from orthodontic brace 810 and installed separately from orthodontic brace 810. In other embodiments a wire may be provided through, along, and/or coupled to orthodontic brace 810.

Various TAD engagement structures and bracket engagement structures are depicted in FIG. 5A through FIG. 5F. One of ordinary skill in the art, having had the benefit of the present disclosure will recognize that in other embodiments an orthodontic brace may be provided with TAD and/or bracket engagement structure that differs in one or more respect from those depicted in FIG. 5A through FIG. 5F. For example, in some embodiments a pad may be incorporated at one or both non-notched ends of an orthodontic brace. Also, for example, in some embodiments the TAD and/or bracket engagement structure may be configured to interface with a particular TAD and/or a particular bracket or bracket element. Also, for example, in some embodiments the TAD engagement structure and the bracket engagement structure may share a substantially similar size, shape, and/or configuration. Also, for example, in some embodiments the TAD engagement structure and the bracket engagement structure may not share a substantially similar size, shape, and/or configuration. For example, in some embodiments an orthodontic brace may have TAD engagement structure from FIG. 5A and bracket engagement structure from FIG. 5D.

Figure 6:
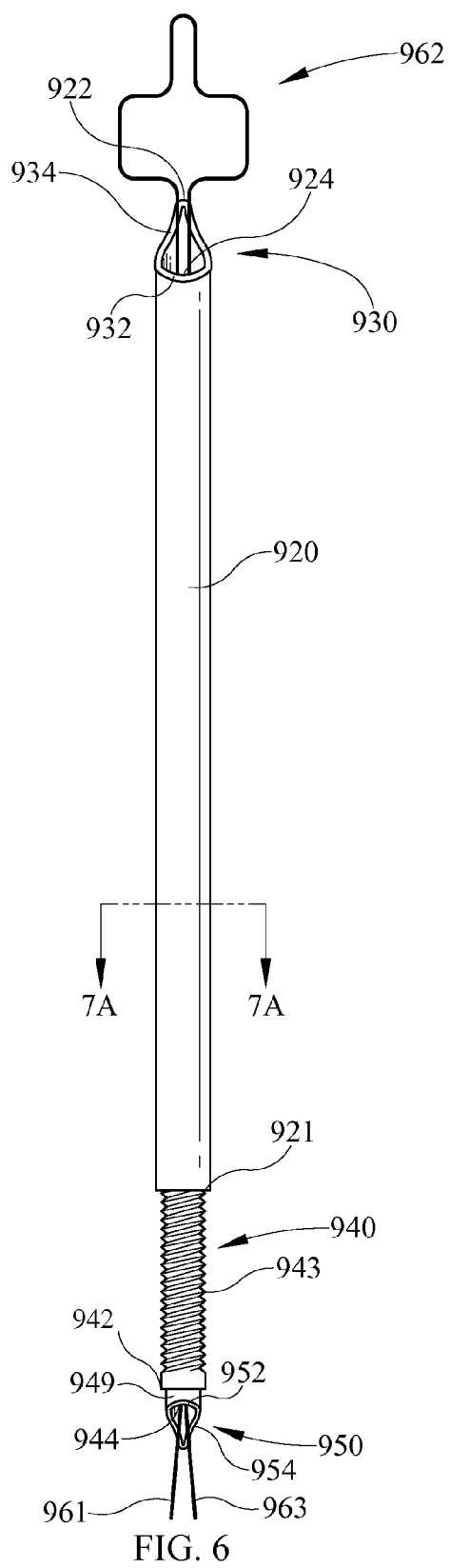
FIG. 6 illustrates a ninth embodiment of an orthodontic brace.

Referring to FIG. 6, a ninth embodiment of an orthodontic brace 910 is illustrated. The orthodontic brace 910 has a rigid outer shaft 920 having a first end 921 and a second end 922. The rigid outer shaft 920 telescopically receives a rigid inner shaft 940 that has a first end (surrounded by rigid outer shaft 920 in FIG. 6) and a second end 942. The rigid inner shaft 940 includes a plurality of threads 943 on an exterior surface thereof. The threads 943 engage corresponding threads on an interior surface of the rigid outer shaft 920. Accordingly, rotating the rigid inner shaft 940 in a first direction relative to the rigid outer shaft 920 will increase the distance between second ends 922 and 942. Conversely, rotating the rigid inner shaft 940 in a second direction relative to the rigid outer shaft 920 will decrease the distance between second ends 922 and 942. Accordingly, a desired fixed position of rigid outer shaft 920 with respect to rigid inner shaft 940 shaft may be achieved through rotational adjustment of rigid inner shaft 940 and/or rigid outer shaft 920. Optionally, in some embodiments a locking nut may be provided around threads 943 to further ensure fixation of the position of rigid outer shaft 920 with respect to rigid inner shaft 940. Also, optionally, in some embodiments a crimp may be utilized to further ensure fixation of the position of rigid outer shaft 920 with respect to rigid inner shaft 940. In alternative embodiments threads 943 may extend along a greater length or shorter length of rigid inner shaft 940.

With continuing reference to FIG. 6, a formed closed loop portion 962 of a wire 960 extends from a wire opening 924 through the second end 922 of rigid outer shaft 920. The wire 960 extends through a wire pathway 960A (FIG. 7A) that extends from wire opening 922 of rigid outer shaft 920 to a wire opening 944 of rigid inner shaft 940. The wire 960 includes a first wire end 961 and a second wire end 963 that extend from the wire opening 944.

A TAD engagement structure 930 is provided proximal to the second end 922 of the rigid outer shaft 920. The TAD engagement structure 930 is formed by the rigid outer shaft 920 and is essentially a cut-out in the rigid outer shaft 920. The TAD engagement structure 930 is shaped to contact and surround TAD 8. The TAD engagement structure 930 includes a notch portion 932 that is integrally formed in the rigid outer shaft 920. The notch portion 932 may contact a TAD when brace 10 is installed. The TAD engagement structure 930 also includes an extension portion 934 that extends from the notch portion 932. The extension portion 934 is integrally formed in the rigid outer shaft 920 and the second end 922 of the rigid outer shaft 920 is at the tip of the extension portion 934. The extension portion 934 and the notch portion 932 may substantially surround a TAD 8 and may reduce the likelihood of complete accidental disengagement of the orthodontic brace 910 from the TAD 8. In the depicted embodiment the wire 960 is not coupled to the TAD engagement structure 930, but simply passes adjacent thereto.

A bracket engagement structure 950 is coupled to the second end 942 of the rigid inner shaft 940. The bracket engagement structure 950 is shaped to contact and surround all or a portion of a bracket. The bracket engagement structure 950 is rotatably coupled to the rigid inner shaft 940 such that when rigid inner shaft 940 is rotated, bracket engagement structure 950 may remain stationary. The bracket engagement structure 950 is coupled to the rigid inner shaft 940 via an extension 949 rotatably received within shaft 940. Extension 949 may include structure within rigid inner shaft 940 that interfaces with corresponding internal structure of rigid inner shaft 940 to substantially prevent vertical movement of extension 949 with respect to rigid inner shaft 940 while enabling rotational movement of extension 949 with respect to rigid inner shaft 940. For example, extension 949 may include an exterior flange sandwiched between interior flanges within rigid inner shaft 940. Also, for example, extension 949 may include a rubber gasket along its periphery in interference fit (but rotatable with force) with extension 949 and with the interior of rigid inner shaft 940. Optionally, the bracket engagement structure 950 may be selectively rotatably coupled to the rigid inner shaft 940 such that the rotational orientation of the bracket engagement structure 950 with respect to the rigid inner shaft 940 may be selectively fixed (e.g., after the orthodontic brace 910 is installed).

The bracket engagement structure 950 is formed by the extension 949 and is essentially a cut-out in the extension 949. The bracket engagement structure 950 includes a notch portion 952 that is integrally formed in the extension 949. The notch portion 952 may contact a bracket when brace 10 is installed. The bracket engagement structure 950 also includes an extension portion 954 that extends from the notch portion 952. The extension portion 954 is also integrally formed in the extension 949. The extension portion 954 and the notch portion 952 may substantially surround all or portion of a bracket and may reduce the likelihood of complete accidental disengagement of the orthodontic brace 910 from the bracket. In the depicted embodiment the wire 960 is not coupled to the bracket engagement structure 950, but simply passes adjacent thereto.

Figures 7A, 7B, 7C, 7D, 7E:
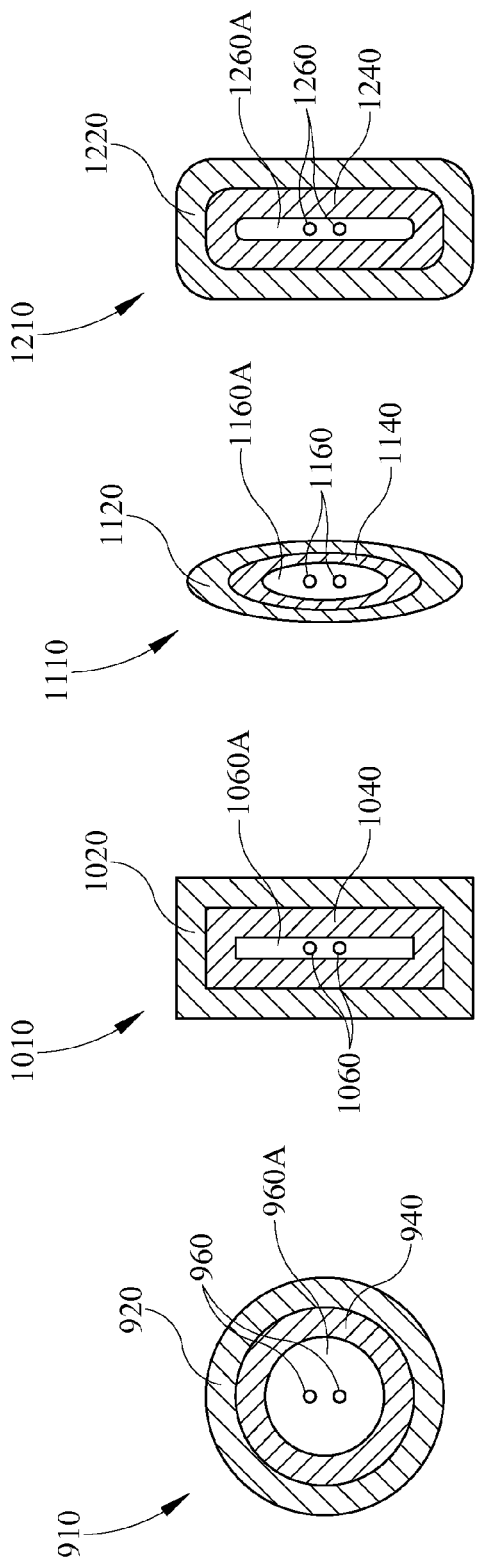
FIG. 7A illustrates a section view of the orthodontic brace of FIG. 6 taken along the section line 7A-7A of FIG. 6
FIG. 7B illustrates a section view of a tenth embodiment of an orthodontic brace.
FIG. 7C illustrates a section view of an eleventh embodiment of an orthodontic brace.
FIG. 7D illustrates a section view of a twelfth embodiment of an orthodontic brace.
FIG. 7E illustrates a section view of a thirteenth embodiment of an orthodontic brace.

FIG. 7A illustrates a section view of the orthodontic brace 910 of FIG. 6 taken along the section line 7A-7A of FIG. 6. The wire pathway 960A through which the wire 960 of orthodontic brace 910 extends is visible in FIG. 7A. In alternative embodiments the wire pathway 960A may be divided into two separate wire pathways. As illustrated in FIG. 7A, the orthodontic brace 910 has a cross-section that is generally circular.

FIG. 7B illustrates a section view of a tenth embodiment of an orthodontic brace 910 having a rigid outer shaft 1020 telescopically receiving a rigid inner shaft 1040. A wire pathway 1060A is interior of rigid outer shaft 1020 and rigid inner shaft 1040 and has a wire 1060 therein. The orthodontic brace 1010 has a cross-section that is generally rectangular.

FIG. 7C illustrates a section view of an eleventh embodiment of an orthodontic brace 1110 having a rigid outer shaft 1120 telescopically receiving a rigid inner shaft 1140. A wire pathway 1160A is interior of rigid outer shaft 1120 and rigid inner shaft 1140 and has a wire 1160 therein. The orthodontic brace 1110 has a cross-section that is generally elliptical.

FIG. 7D illustrates a section view of a twelfth embodiment of an orthodontic brace 1210 having a rigid outer shaft 1220 telescopically receiving a rigid inner shaft 1240. A wire pathway 1260A is interior of rigid outer shaft 1220 and rigid inner shaft 1240 and has a wire 1260 therein. The orthodontic brace 1210 has a cross-section that is generally rectangular with rounded corners.

FIG. 7E illustrates a section view of a thirteenth embodiment of an orthodontic brace 1310 having a generally C shaped rigid outer shaft 1320 telescopically receiving a generally C shaped rigid inner shaft 1340. A wire pathway 1360A is interior of rigid outer shaft 1320 and rigid inner shaft 1340 and has a wire 1360 therein. In the embodiment of FIG. 7E the rigid inner shaft 1340 and the rigid outer shaft 1320 do not completely surround the wire pathway 1360A. Rather, the rigid inner shaft 1340 and the rigid outer shaft 1320 define a longitudinally extending opening 1368 that provides access to the wire pathway 1360A. In use, the wire 1360 may optionally be independently coupled to a TAD and bracket within a patient's mouth prior to being placed within the wire pathway 1360A. After the coupling of the wire 1360, the orthodontic brace 1310 may be placed over the wire 1360 and fixedly adjusted to appropriately engage the TAD and bracket within a patient's mouth.

Various cross-sectional shapes of an orthodontic brace are depicted in FIG. 7A through FIG. 7E. One of ordinary skill in the art, having had the benefit of the present disclosure will recognize that in other embodiments an orthodontic brace may have another cross-sectional shape that differs in one or more respect from the cross sectional shapes depicted in FIG. 7A through FIG. 7E.

Although a wire pathway extending interiorly of the shaft portion of a brace has been described and depicted herein, in alternative embodiments a brace may be provided without a wire pathway extending interiorly of the shaft portion thereof and/or with an alternative wire pathway. For example, in some embodiments a wire pathway may be provided exteriorly of the shaft portion of the brace. Also, for example, in some embodiments a first wire pathway may carry a first wire portion and a second wire pathway may carry a second wire portion. The first wire portion and the second wire portion may form part of the same wire or may be two distinct wires. Also, for example, in some embodiments a first wire portion may be provided and may be anchored to the brace (exteriorly or interiorly of the brace) and a separate second wire portion may also be provided and anchored to the brace (exteriorly or interiorly of the brace).

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An orthodontic brace for use in conjunction with an orthodontic bracket and an orthodontic temporary anchorage device, said orthodontic brace comprising:
   a rigid shaft portion having a shaft first end, a shaft second end, a shaft length extending from said shaft first end to said shaft second end, and at least one interior wire pathway extending from a first opening proximal said shaft first end to a second opening proximal said shaft second end; wherein said shaft length is fixedly adjustable to a desired length of a plurality of lengths;
   a continuous malleable wire extending through said at least one interior wire pathway, said malleable wire having a first wire portion extending beyond said first opening and a second wire portion extending beyond said second opening, wherein said malleable wire is freely movable relative to said rigid shaft portion, and wherein said first wire portion is a closed loop portion and said second wire portion includes a first wire end and a second wire end;
   a temporary anchorage device engagement structure proximal said shaft first end, said temporary anchorage device engagement structure having at least one temporary anchorage device notch and being sized and configured to engage said temporary anchorage device; and
   an orthodontic bracket engagement structure proximal said shaft second end, said orthodontic bracket engagement structure having at least one orthodontic bracket notch and being sized and configured to engage said orthodontic bracket.

2. The orthodontic brace of claim 1 wherein said rigid shaft portion includes a rigid outer shaft telescopically receiving a rigid inner shaft.

3. The orthodontic brace of claim 2 wherein at least a portion of said rigid outer shaft is interiorly threaded and at least a portion of said rigid inner shaft is exteriorly threaded.

4. The orthodontic brace of claim 2 wherein said rigid outer shaft is crimpable.

5. The orthodontic brace of claim 1 wherein said at least one interior wire pathway extends from said shaft first end to said shaft second end.

6. The orthodontic brace of claim 1 wherein said rigid shaft portion does not completely surround said at least one interior wire pathway.

7. A system for bidirectionally bracing an anchor tooth, comprising:
   an orthodontic bracket adapted to temporarily fix to tooth structure;
   an orthodontic temporary anchorage device adapted to temporarily fix to bone structure;
   a brace having a rigid shaft portion with a first end and a second end, a temporary anchorage device engagement structure at said first end, and an orthodontic bracket engagement structure at said second end;
   said rigid shaft portion having a shaft length extending from said first end to said second end;
   wherein said shaft length is fixedly adjustable to a desired length of a plurality of lengths;
   wherein said temporary anchorage device engagement structure is adjustable concurrent with said first end and is sized and configured to engage said orthodontic temporary anchorage device; and
   wherein said orthodontic bracket engagement structure is adjustable concurrent with said second end and is sized and configured to engage said orthodontic bracket.

8. The system of claim 7 wherein said temporary anchorage device engagement structure includes at least one temporary anchorage device engagement structure notch.

9. The system of claim 8 wherein said temporary anchorage device engagement structure includes an extension portion extending from said at least one temporary anchorage device engagement structure notch in a direction away from said second end, said extension portion and said at least one temporary anchorage device engagement structure notch sized and configured to substantially surround said orthodontic temporary anchorage device.

10. The system of claim 7 wherein said system further comprises a wire freely movable relative to said brace.

11. The system of claim 10 wherein said rigid shaft portion has a wire pathway extending therethrough, said wire pathway partially housing said wire.

12. The system of claim 11, wherein said wire pathway extends from said first end to said second end of said rigid shaft portion.

13. The system of claim 7 wherein said rigid shaft portion includes a rigid outer shaft telescopically receiving a rigid inner shaft.

14. The system of claim 7 wherein said orthodontic bracket includes an orthodontic bracket hook and wherein said orthodontic bracket engagement structure is sized and configured to engage said orthodontic bracket hook.

15. A method of bidirectionally anchoring an anchor tooth, comprising:
    selecting a brace having a brace first end, a brace second end, and an adjustable length;
    securing a first wire portion in contact with a temporary anchorage device coupled to boney structure of a patient;
    securing a second wire portion in contact with an orthodontic bracket coupled to a tooth of said patient;
    fixedly adjusting said adjustable length of said brace to a set length;
    wherein when said brace is at said set length, said brace is additionally in contact with said orthodontic bracket at said first end and with said temporary anchorage device at said second end and substantially prevents movement of said orthodontic bracket in a first direction;
    wherein said second wire portion secured to said orthodontic bracket is substantially taut and said first wire portion secured to said temporary anchorage device is substantially taut; and
    wherein said first wire portion and said second wire portion substantially prevent movement of said orthodontic bracket in a second direction that is substantially opposite of said first direction.

16. The method of claim 15 wherein said first wire portion extends from said brace when said first wire portion is secured to said temporary anchorage device.

17. The method of claim 15 wherein said brace includes an outer shaft telescopically receiving an inner shaft.

18. The method of claim 17 wherein said set length of said brace is fixedly adjusted following securing of said first wire portion to said temporary anchorage device and securing of said second wire portion to said orthodontic bracket.

19. The method of claim 15 wherein said first wire portion and said second wire portion are part of a single wire and extend through at least a portion of said brace.

* * * * *